United States Patent
Huang (10) Patent No.: US 10,695,759 B2
(45) Date of Patent: Jun. 30, 2020

(54) MICROFLUIDIC REAGENT CARD AND DETECTION METHOD AND APPLICATION THEREOF

(71) Applicant: TIANJIN DEXIANG BIOTECHNOLOGY CO., LTD., Tianjin (CN)

(72) Inventor: Zhigang Huang, Tianjin (CN)

(73) Assignee: TIANJIN DEXIANG BIOTECHNOLOGY CO., LTD., Tianjin (CN)

( * ) Notice: Subject to any disclaimer, the term of this patent is extended or adjusted under 35 U.S.C. 154(b) by 0 days.

(21) Appl. No.: 16/318,275

(22) PCT Filed: Dec. 30, 2016

(86) PCT No.: PCT/CN2016/113508
§ 371 (c)(1),
(2) Date: Jan. 16, 2019

(87) PCT Pub. No.: WO2018/014513
PCT Pub. Date: Jan. 25, 2018

(65) Prior Publication Data
US 2019/0283018 A1  Sep. 19, 2019

(30) Foreign Application Priority Data

Jul. 18, 2016 (CN) .......................... 2016 1 0562969

(51) Int. Cl.
*B01L 3/00* (2006.01)
*C12M 3/06* (2006.01)
*G01N 33/577* (2006.01)

(52) U.S. Cl.
CPC .............. *B01L 3/5027* (2013.01); *B01L 3/00* (2013.01); *C12M 23/16* (2013.01);
(Continued)

(58) Field of Classification Search
CPC .......... B01L 3/5027; B01L 3/502; B01L 3/50; C12M 23/16; C12M 23/02; C12M 23/00
(Continued)

(56) References Cited

U.S. PATENT DOCUMENTS 7,534,618 B2 * 5/2009 Tyvoll ............... B01L 3/502753
422/72
2002/0097632 A1 * 7/2002 Kellogg ............... B01F 5/0647
366/220
(Continued)

FOREIGN PATENT DOCUMENTS

CN   101118239 A   2/2008
CN   201397336 Y   2/2010
(Continued)

OTHER PUBLICATIONS

English Machine Translation of CN 101118239 abstract, claim and description. Obtained on Jul. 23, 2019. (Year: 2019).*
(Continued)

*Primary Examiner* — Christine T Mui
(74) *Attorney, Agent, or Firm* — Joseph G. Chu; Jeremy I. Maynard; JCIP (57) ABSTRACT

A microfluidic reagent card for medical testing and assaying is disclosed. The microfluidic reagent card comprises a card body (10) and a plurality of micropipes, the plurality of micropipes is fixed onto the card body (10). The plurality of micropipes is arranged radially. Each of the micropipe is configured to have a sample inlet end (1) and a closed end (2), and a detection liquid layer (3) and a separation medium layer (4) are arranged inside each micropipe in sequence from the sample inlet end (1) to the closed end (2). The micropipe has a diameter of 0.1-1.0 mm. As the micropipe is configured to have a small diameter, the fluidity of liquid and gel decreases inside the micropipe, and the liquid interface will not flow even when the micropipe is placed in a horizontal direction.

7 Claims, 3 Drawing Sheets

(52) U.S. Cl.
CPC ...... *G01N 33/577* (2013.01); *B01L 2200/025* (2013.01); *B01L 2200/0668* (2013.01); *B01L 2300/0816* (2013.01)

(58) Field of Classification Search
USPC .......................................... 422/502, 500, 50
See application file for complete search history.

(56) References Cited

U.S. PATENT DOCUMENTS

2004/0096960 A1* 5/2004 Burd Mehta ........ C12Q 1/6874
435/287.2
2012/0276641 A1* 11/2012 Dimov ................ B01L 3/50273
436/63

FOREIGN PATENT DOCUMENTS

| CN | 101701961 A | 5/2010 |
| CN | 205353104 U | 6/2016 |
| CN | 106076445 A | 11/2016 |
| EP | 2233210 A1 | 9/2010 |

OTHER PUBLICATIONS

International Search Report and Written Opinion of International Search Authority for International Application No. PCT/CN2016/113508, dated Apr. 26, 2017, pp. 1-4.

* cited by examiner

MICROFLUIDIC REAGENT CARD AND DETECTION METHOD AND APPLICATION THEREOF

TECHNICAL FIELD

The present invention is related to the technical field of medical testing/assay techniques, in particular a microfluidic reagent card and its detection method and applications.

BACKGROUND

With the rapid development of the world's biological engineering technology, detection and identification methods for cross-matching of blood, blood type and antibodies, have gradually shifted from the traditional serological routine testing to micropipe gel immunoassay technology. Micropipe gel immunoassay detection methods need to be used with a micropipe reagent card. At home and abroad, some manufacturers produce ABO blood typing and Rh stereotyped ABO/Rh blood typing detection reagent card, but the gel used is Sephadex, the diameter of Sephadex particles is about 20-50 microns. Blood type reagent card generally comprises six or eight micropipe gel pipes, which are fixed side by side and uniformly distributed on a transparent polypropylene plastic card. Each micropipe gel pipe comprises an upper large pipe, an intermediate transition pipe, and a bottom small pipe, which are connected together. Each micropipe gel pipe is equipped with gel that functions to separate red blood cells. During the course of detection, one or two of the different samples or reagents are usually dribbled into the large upper pipe, and then reagent card is placed into a centrifuge. After centrifugation, the results are interpreted by naked eyes or with a camera system. Sample loading, centrifugation and photography of result are carried out at three different devices. The centrifugation is done in a horizontal manner, and the different micropipes are arranged in parallel. As the sample is loaded in a vertical manner, the centrifugation is conducted in a horizontal manner, and the results need to be read in a vertical manner, one need to either use a hand or a mechanical gripper to perform multiple operations to move the reagent card.

Patent Application No. 201110318663.4 discloses a blood type reagent card, the card comprises a card body and six micropipe gel pipes, each micropipe gel pipe is made by an upper large pipe, an intermediate transition pipe, and a bottom small pipe, the inner side of the intermediate transition pipe is formed by connecting a disc hole and a tapered hole together. The disc hole is connected to the upper large pipe; the tapered hole is connected to the bottom small pipe; the major diameter of the disc hole is the same as the diameter of the upper large pipe, the minor diameter of the disc hole is the same as that of the tapered hole; the major diameter of the tapered hole is the same as the diameter of the bottom small pipe.

Patent Application No. 201110322294.6 discloses an ABO/Rh blood type reagent card and a preparation method thereof for newborns, the card comprises eight micropipe gel pipes: a gel pipe containing IgM monoclonal anti-A antibody, a gel pipe containing IgM monoclonal anti-B antibody, a gel pipe containing IgM monoclonal anti-AB antibody, a gel pipe containing IgM monoclonal anti-D, a gel pipe containing IgM and IgG monoclonal anti-D antibody, a gel pipe containing gel suspension medium for negative control, a gel pipe containing an anti-IgG reagent and a gel pipe containing an anti-C3d reagent.

Patent Application No. 201510483054.2 discloses an IgG subtype classification detection reagent card and a preparation method thereof, comprising the following six steps: preparation of gel suspension medium, screening of Sephacryl gel, selection of antibodies, preparation of the gel containing anti-IgG antibody, subpackaging and sealing for preservation.

The inner diameter of the existing reagent card is relatively large, between 2-4 mm. The liquid interface has high fluidity. The reagent cards therefore need to be strictly placed in a vertical manner during transportation to avoid shocks. Otherwise, such shocks might cause a splash of the liquid and even the gel, significantly affecting results of reagent testing. The existing reagent cards are typically required to be centrifuged before detection to restore the distribution of the liquid and the separation medium. The existing method requires the reagent card to be placed vertically during sample loading, the reagent needs to be added to each hole individually. During centrifugation, the card needs to be placed in a vertical manner and centrifuged with a horizontal rotor. After centrifugation, the card is shifted from the centrifuge to an interpretoscope to interpret the results. Thus, uneven rotor can cause uneven centrifugal interface and accordingly affect the result interpretation. The reagent card needs to be placed vertically on the loading platform during operation, transferred from the loading platform to the centrifugal platform. The reagent card needs to be placed in a vertical manner for centrifugation. The reagent card goes horizontal during centrifugation and goes back to the vertical direction after centrifugation. Thereafter the reagent card is shifted to the interpretoscope for result interpretation. The reagent card needs to be frequently changed among the three platforms and between two orientations, which complicates the operation. In centrifugation, reagent card plane and centrifugal plane are placed vertically, during the course of centrifugation, the reagent card is driven by centrifugal force and rotated by 90 degrees. The micropipe and the centrifugation plane become parallel. A plurality of micropipes is arranged in parallel.

SUMMARY OF INVENTION

Accordingly, the present invention discloses a microfluidic reagent card and a detection method and application thereof. A micropipe of the microfluidic reagent card is configured to have a small diameter, which significantly reduces the fluidity of liquid and gel, so that a liquid interface does not flow even when the micropipe is placed in a horizontal manner. During the course of sample addition, centrifugation and result interpretation of the microfluidic reagent card, the microfluidic reagent card can be kept in a horizontal manner without being vertically placed. The liquid inside the micropipe can be kept at a fixed interface, and the interface formed by a separation medium is not likely to be stirred easily, thereby facilitating transportation and accurate result determination.

To achieve the above objects, the technical solution of the present invention discloses:

A micropipe, the micropipe is configured to have a sample inlet end and a closed end, a detection liquid layer and a separation medium layer are arranged inside each of the micropipe in sequence from the sample inlet end to the closed end, the micropipe has a diameter of 0.1-1.0 mm.

Preferably, the micropipe has a length of 8-12 mm.

Preferably, the cross section of the micropipe is in general configured to have a circular or elliptical shape and may also be configured to have a square or rectangular shape, as long as the structure of the cross section is closed.

Preferably, the micropipe has a diameter of 0.8 mm.

As the diameter of the micropipe is small, the fluidity of liquid and gel is significantly reduced. Thus, a liquid interface does not flow even when the micropipe is placed in a horizontal manner, i.e., the liquid in the capillary can maintain a fixed interface. As the diameter of the micropipe that holds the liquid decreases, due to siphoning and capillarity effects, the interface of the liquid gets more stable, thus, the liquid does not flow out even when the micropipe is placed upside down, and the interface of the liquid is still maintained. The liquid in the capillary does not flow easily during the course of detection, the interface formed by the separation medium is not easily stirred. Thus, the problem of liquid splashing during transportation can be effectively mitigated.

Further, the sample is loaded into each of the micropipe separately through the sample inlet end of each of the micropipe, or the sample is loaded into a plurality of micropipes through the sample inlet end connected to an automatic quantitative sample distribution device. The plurality of micropipes is integrated with the automatic quantitative sample distribution device, which enables sample loading at one go for multiple detections, as well as obtaining multiple detection results in parallel. As the automatic quantitative sample distribution device makes use of the capillary and siphon mechanisms to take in the sample, the process of sample addition and distribution can be done on a horizontal plane.

Further, the separation medium layer is made of gel particles or glass beads.

Preferably, the gel particles are modified with antibody or unmodified, the gel particles can be made of glucan, cellulose and other different materials, and the gel particles mainly function to isolate single cells and agglutinated cells. Protein G or protein A can also be used to modify the surface of the separation medium layer, enabling the separation medium layer to absorb sensitized red blood cells. The separation medium layer is made of generally circular or nearly circular particles, which can function to block the agglutinated red blood cells and allow the non-agglutinated red blood cells to pass.

Further, the detection liquid layer comprises a diluent, the diluent comprises an antibody reagent or does not comprises any antibody reagent.

Preferably, the antibody reagent is anti-A reagent or anti-B reagent or anti-Rh(D) reagent or anti-human IgG antibody, but not limited to these antibody reagents.

Preferably, the antibody diluent is a buffer containing 1% BSA and 0.1% sodium azide.

The second purpose of the present invention is to provide a microfluidic reagent card, which comprises a card body and the micropipe, and the micropipe is fixed onto the card body.

Further, the microfluidic reagent card comprises one micropipe or a plurality of micropipes, the plurality of micropipes is arranged radially, the closed end of the micropipe is arranged at the lateral side of the micropipe. The plurality of micropipes is radially distributed according to the center of centrifugation on a plane.

Further, the microfluidic reagent card also comprises an automatic quantitative sample distribution device, the plurality of micropipes is connected to the automatic quantitative sample distribution device, which comprises a sample adding component and a plurality of quantitative sample distribution systems.

The automatic quantitative sample distribution device is used to quantitatively distribute the sample (such as whole blood or diluted red blood cells) into multiple reaction chambers at one go after the sample is added once by microfluidic technology, so that multiple detections can be conducted in parallel. A predetermined amount of sample is entered into the connected micropipe, the separation medium layer of the micropipe separates agglutinated from non-agglutinated materials (red blood cells).

The microfluidic reagent card comprises an automatic quantitative sample distribution device and a micropipe gel separation device; the automatic quantitative sample distribution device comprises a sample adding component and a plurality of quantitative sample distribution systems, the micropipe gel separation device is used to separate agglutinated from non-agglutinated red blood cells. A predetermined amount of sample enters into the connected micropipe gel separation device, which separates agglutinated from non-agglutinated red blood cells. The automatic quantitative sample distribution devices are arranged in a ring, each of the automatic quantitative sample distribution device is connected to a plurality of micropipes, the plurality of micropipes is arranged radially, and the closed end of the micropipe is arranged at the lateral side of the micropipe.

Preferably, the automatic quantitative sample distribution device of the microfluidic reagent card comprises a sample adding component, the sample adding component is connected to a quantitative region, the quantitative region is connected to the sample inlet end of the micropipe, a closing portion is provided between the quantitative region and the sample inlet end of the micropipe; the micropipe is connected to the automatic quantitative sample distribution device, which enables adding the sample at one go for multiple detections, and obtaining multiple detection results in parallel.

Preferably, a pathway between the quantitative region and the closing portion gradually narrows, the pathway between the closing portion and the sample inlet end is narrower than the pathway in front of the closing portion; the pathway in front of the closing portion has a diameter of 0.08-0.14 mm, the pathway between the closing portion and the sample inlet end has a diameter of 0.15-0.3 mm.

As the size of the pathway of the automatic quantitative sample distribution device changes, it facilitates the capillarity and siphoning effects for sample addition, so that sample addition and sample distribution can be conducted on a plane.

Preferably, the micropipe and/or the automatic quantitative sample distribution device is equipped with an exhaust passage. In use, the exhaust passage is open to the external atmosphere, can therefore function to balance air pressure during the course of sample addition, which could facilitate the process of sample addition. The exhaust passage ensures the flow of reagent fluid inside the micropipe.

The liquid and gel in the microfluidic reagent card of the present invention can maintain a fixed interface when the microfluidic reagent card is placed horizontally. The microfluidic reagent card can be kept horizontally during the course of sample addition and centrifugation, without being vertically placed. This accordingly enables the microfluidic reagent card to be placed horizontally onto a centrifuge for centrifugation. The micropipes of the microfluidic reagent card of the present invention are radially distributed, so that the centrifugation can be conducted on a horizontal plane. Meanwhile, the microfluidic reagent card is connected to an automatic quantitative sample distribution device, which allows the sample addition to be completed at one time, and the distribution of the sample can be conducted automatically. This reduces the operations required during the course of sample addition. The automatic quantitative sample distribution device of the present invention also has the function of quantitative sample distribution, making it unnecessary for user to load sample very accurately during the course of sample addition.

The third purpose of the invention is to provide a detection method using the microfluidic reagent card, comprising the following steps: enter the sample into the micropipe to be mixed with the detection liquid layer, centrifuge the microfluidic reagent card, and read result from the microfluid reagent card. The method of the sample addition can be conducted in a horizontal manner. The centrifugation and result reading can also be carried out on a horizontal plane.

The sample distribution system adds sample by siphoning and capillarity effects, thus the sample addition and sample distribution can be conducted on a horizontal plane. In this way, the microfluidic reagent card can be kept horizontally during the course of sample addition and centrifugation, without being vertically placed. Photography of result can be carried out on the horizontal plane in the late stage, significantly improving the convenience of operation, simplifying the construction of the automatic instruments. Thus, the present invention is efficient, convenient and cost-effective. The design of the present invention also reduces the size of the microfluidic reagent card, the formation of a stable interface eases the transportation requirements, accordingly reducing the transportation costs significantly and improving the stability of the reagent.

The other purpose of the invention is to provide an application of the micropipe or microfluidic reagent card in antigen-antibody detection.

Further, the application is selected from a group consisting of blood grouping, antibody screening and cross-matching of blood.

The micropipe or the microfluidic reagent card of the present invention can be used in blood grouping, antibody screening and cross-matching of blood. During detection, the liquid in capillaries does not flow easily, and the interface formed by the separation medium is not stirred easily, thereby facilitating accurate result determination. Loading sample through multiple micropipes simultaneously enables adding sample once for multiple detections, which can achieve multiple test results and improve the accuracy of result determination.

The technical advantages of the present invention are:
1. As the micropipe diameter of the present invention is small, the fluidity of liquid and gel is reduced significantly, so that, even when the micropipe is placed in a horizontal manner, the liquid interface does not flow, i.e., the liquid in the capillary can maintain a fixed interface.
2. The sample inlet end of the micropipe is connected to an automatic quantitative sample distribution device, which enables simultaneous sample addition, simultaneous detections of multiple samples, and achieving multiple test results. This therefore simplifies the operation of the detection.
3. The microfluidic reagent card of the present invention comprises one or more micropipes configured to have a small diameter. As the sample is added by capillarity and siphoning mechanisms, during the course of sample addition and centrifugation, the microfluidic reagent card can be kept horizontally, without being vertically placed. The photography of result can be carried out on a horizontal plane in the late stage of the detection, significantly improving the convenience of operation, simplifying the components of the automatic instruments. Accordingly, the present invention is efficient, convenient and cost-effective. The microfluidic reagent card is configured to be connected to an automatic quantitative sample distribution device, which enables adding sample at one time, distributing sample automatically, reducing operations during sample addition. The automatic quantitative sample distribution device of the present invention also has the function of quantitative sample distribution, thus accurate sample addition is not required.
4. As the liquid inside the microfluidic reagent card does not flow easily, the problem of liquid splashing can be effectively mitigated during transportation. The interface formed by the separation medium is not likely to be easily stirred, thereby facilitating transportation and accurate result determination.
5. This design of the microfluidic reagent card also reduces the size of the reagent card. The stable interface accordingly eases transportation requirements, which substantially reduces transportation cost and improves the stability of the reagent.

DRAWINGS

FIG. 1 illustrates a micropipe structure of Embodiment 1 of the present invention. Reference number: 1—sample inlet end, 2—closed end, 3—detection liquid layer, 4—separation medium layer.

FIG. 2 illustrates a micropipe structure of Embodiment 2 of the present invention. Reference number: 1—sample inlet end, 2—closed end, 3—detection liquid layer, 4—separation medium layer, 5 quantitative region, 6 closing portion, 7 exhaust passage.

FIG. 3 illustrates a micropipe structure of Embodiment 3 of the present invention. Reference number: 1—sample inlet end, 2—closed end, 3—micropipe, 5 quantitative region, 6 closing portion, 7—exhaust passage, 8—sample adding component, 9—overflow region.

EMBODIMENTS

The following is a detailed description of the preferred embodiments of the present invention, in conjunction with the attached drawings. Experimental methods without specific conditions indicated in the preferred embodiments are usually conducted under normal conditions. The embodiments are provided to better illustrate the specifics of the invention, but they are not limited the invention to the embodiments. Thus, modifications and adaptations to the foregoing embodiments of the present invention conceived by those skilled in the art shall still fall within the scope of the present invention.

Embodiment 1

Figure 1:
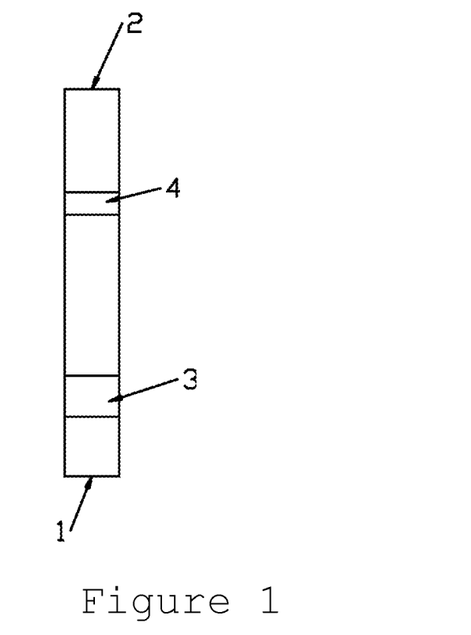

A micropipe as illustrated in FIG. 1, wherein the micropipe is configured to have a sample inlet end 1 and a closed end 2, a detection liquid layer 3 and a separation medium layer 4 are arranged inside the micropipe in sequence from the sample inlet end 1 to the closed end 2. The micropipe has a diameter of 0.8 mm, and a length of 10 mm.

Separation using the micropipe of the present embodiment: a micropipe gel separation device is used to separate agglutinated from non-agglutinated red blood cells. A predetermined amount of sample is entered into the connected micropipe gel separation device, separating agglutinated from non-agglutinated red blood cells.

When the sample enters into the micropipe and passes through the detection liquid layer, the sample reacts with the detection liquid layer, and then contacts the separation medium layer, which functions to separate and determine the reactants. The small diameter of the micropipe saves the use of sample and reagents, as well as substantially reduces the fluidity of liquid and gel, so that liquid interface does not flow even when the micropipe is placed in a horizontal direction, i.e., the liquid in the capillary can maintain a fixed interface.

Embodiment 2

Figure 2:
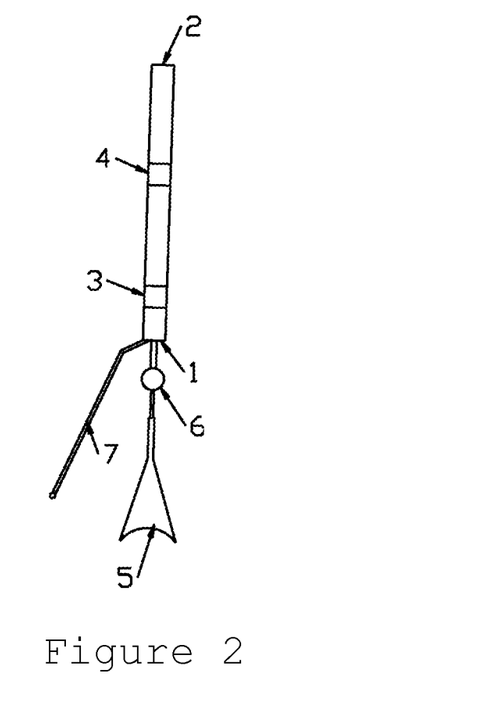

See Embodiment 1, according to the micropipe shown in FIG. 2, the micropipe is configured to have a sample inlet end 1 and a closed end 2, a detection liquid layer 3 and a separation medium layer 4 are arranged inside the micropipe in sequence from the sample inlet end to the closed end. The micropipe has a diameter of 0.8 mm, and a length of 10 mm. The sample inlet end 1 and a quantitative region 5 are connected. A closing portion 6 is provided between the sample inlet end 1 and the quantitative region 5, and the closing portion 6 is filled with sealing material. After the sample enters into the quantitative region 5, unseal the sealing material. Any material that can function to seal and unseal the closing portion 6 is suitable for the present invention. For example, the present embodiment utilizes paraffin wax to seal the closing portion. After the sample is loaded, the paraffin wax can be melted by warm light, accordingly allowing the sample to enter the micropipe. To ensure the fluidity of the sampling solution, the sample inlet end is configured to have an exhaust passage 7.

The pathway between the quantitative region 5 and the closing portion 6 gradually narrows, the pathway between the closing portion 6 and the sample inlet end 1 is narrower than the pathway in front of the closing portion. The diameter of the pathway in front of the closing portion 6 is 0.08-0.14 mm, the diameter of the pathway between closing portion 6 and sample inlet end 1 is 0.15-0.3 mm. Specifically, the pathway in front of the closing portion 6 has a diameter of 0.1 mm, the pathway between the closing portion 6 and the sample inlet end 1 has a diameter of 0.2 mm.

The micropipe of the present embodiment comprises an automatic quantitative sample distribution device. The micropipe is configured to be connected to the automatic quantitative sample distribution device, which comprises a sample adding component and a plurality of quantitative sample distribution systems. The micropipe gel separation device is used to separate agglutinated from non-agglutinated red blood cells. A predetermined amount of sample enters into the connected micropipe gel separation device, which separates agglutinated from non-agglutinated red blood cells.

Embodiment 3

Figure 3:
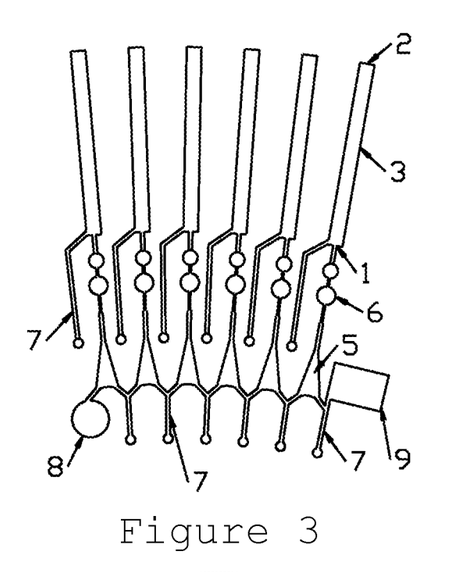

See Embodiment 2, according to the micropipe shown in FIG. 3, a sample inlet end 1 of the micropipe 3 is connected to an automatic quantitative sample distribution device. The automatic quantitative sample distribution device is connected to a plurality of micropipes 3. The automatic quantitative sample distribution device comprises a sample adding component and a plurality of quantitative sample distribution systems.

Specifically, the present embodiment provides six micropipes 3, which are connected to the automatic quantitative sample distribution device, the sample adding component of the automatic quantitative sample distribution device is configured to take the form of a sample adding region 8, which is connected to the quantitative sample distribution system. The quantitative sample distribution system of the present embodiment comprises six quantitative regions 5 (the number of the quantitative regions correspond to the number of micropipes). The sample adding region 8 is connected to the quantitative region 5. Among the six quantitative regions 5, the furthest from the sample adding region 8 is connected to an overflow region 9. After adding sample into the sample adding region 8, the sample will fill up the six quantitative region 5 from the nearest to the furthest. Once the quantitative region 5 furthest from the sample adding region 8 is filled up, the sample will enter into the overflow region 9. The setting of the overflow region 9 is configured to facilitate easy observation once the overflow region 9 has been filled up once the sample enters into the overflow region 9, it means that the quantitative regions 5 have been fully filled up. Due to the small size of the whole device, in order to avoid any obstruction caused by atmospheric pressure, an exhaust channel 7 is arranged between each two of the quantitative regions 5. Similarly, both the overflow region 9 and the sample inlet end 1 are arranged to have an exhaust channel 7. All of the quantitative regions 5 are configured to have the same size, and to accommodate the same amount of sample, which is to ensure uniformity in the quantities of the experiments. Each quantitative region 5 is connected to the sample inlet end 1 of the micropipe 3 through a pipe. The closing portion 6 is provided in the micropipe, so that the sample and the reagent inside the micropipe do not mix under normal condition.

Embodiment 4 A Human ABO Blood Group Positive Typing and Rh(D) Blood Group Microfluidic Reagent Card A human ABO blood group positive typing and Rh(D) blood group microfluidic reagent card comprises a card body and a plurality of micropipe, and the plurality of micropipe are fixed onto the card body. The plurality of the micro cubes is divided into 12 groups, each group has 4 micropipes. The plurality of micropipes is arranged radially, and radially distributed according to the center of centrifugation on a plane. The microfluidic reagent card further comprises an automatic quantitative sample distribution device, the micropipe is connected to the automatic quantitative sample distribution device. The automatic quantitative sample distribution device comprises a sample adding component and a plurality of quantitative sample distribution systems. The micropipe gel separation device is used to separate agglutinated from non-agglutinated red blood cells. A predetermined amount of sample enters into the connected micropipe gel separation device, which separates agglutinated from non-agglutinated red blood cells.

The separation medium layer in the micropipe are gel particles.

The detection liquid layers in each group of 4 micropipes are:

| Micropipe No. | Component Description |
| --- | --- |
| Micropipe 1: anti-A reagent | anti-A mouse monoclonal (IgM) antibody (clone BRIMA-1) |
| Micropipe 2: anti-B reagent | anti-B mouse monoclonal (IgM) antibody (clone LB-2) |

| Micropipe No. | Component Description |
|---|---|
| Micropipe 3: anti-Rh(D) reagent | Anti-Rh(D) human monoclonal (IgM) antibody (clone RUM-1) |
| Micropipe 4: antibody diluent | Diluent, no antibody |

Figure 4:
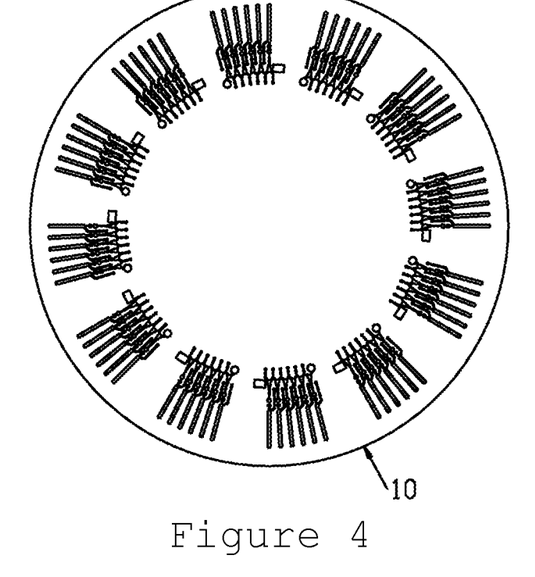
FIG. 4 illustrates a microfluidic reagent card structure of Embodiment 5. Reference number: 10—card body.

Embodiment 5 Human ABO-positive/Reverse Group and Rh (D) Blood Group Microfluidic Reagent Card A human ABO-positive/reverse group and Rh (D) blood group microfluidic reagent card, with reference to FIG. 4, comprises a card body and a plurality of micropipes, the plurality of micropipes is fixed on the card body. The plurality of micropipes 12 are divided into 12 groups, each group has 6 micropipes, the plurality of micropipes is arranged radially, and radially distributed according to the center of centrifugation on a plane. The microfluidic reagent card also comprises an automatic quantitative sample distribution device. The micropipe is connected to an automatic quantitative sample distribution device. The automatic quantitative sample distribution device comprises a sample adding component and a plurality of quantitative sample distribution systems. A micropipe gel separation device is used to separate agglutinated from non-agglutinated red blood cells. A predetermined amount of sample enters into the connected micropipe gel separation device, which separates agglutinated from non-agglutinated red blood cells.

The separation medium layer in the micropipe are gel particles.

The detection liquid layers in each group of 6 micropipes are:

| Micropipe No. | Component Description |
|---|---|
| Micropipe 1: anti-A reagent | anti-A mouse monoclonal (IgM) antibody (clone BRIMA-1) |
| Micropipe 2: anti-B reagent | anti-B mouse monoclonal (IgM) antibody (clone LB-2) |
| Micropipe 3: anti-Rh(D) reagent | Anti-Rh(D) human monoclonal (IgM) antibody (clone RUM-1) |
| Micropipe 4: control reagent | Antibody diluent |
| Micropipe 5, 6: reverse buffer | Antibody diluent |

Reagent to be used together: as verified, "human ABO blood reverse group red blood cell kit (each box contains one A1, B and O reagent, 10 ml/unit)" produced by Shanghai blood biomedical Limited Liability Company, is suitable for the microfluidic reagent card of the present invention.

Embodiment 6

Figure 5:
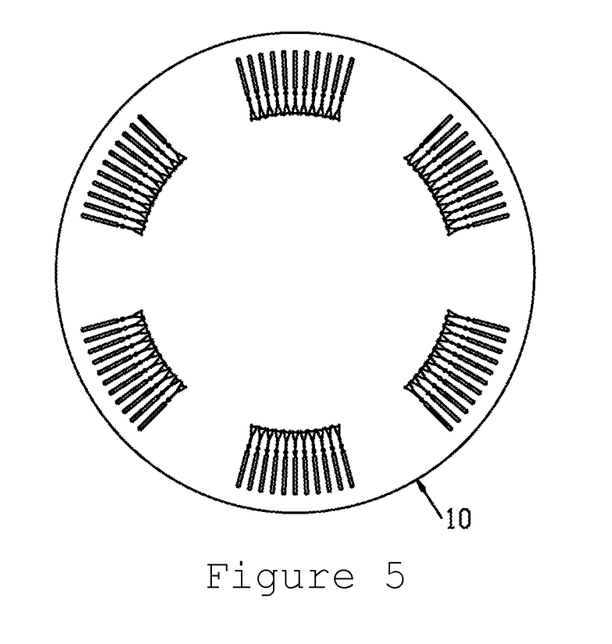
FIG. 5 illustrates a microfluidic reagent card structure diagram of Embodiment 6. Reference number: 10—card body.

FIG. 5 illustrates a microfluidic reagent card, a plurality of micropipes of embodiment 2 are fixed onto a card body 10.

Specifically, there are 6 micropipe groups fixed onto the card body that has a circular shape, each of the 6 micropipe groups has 11 micropipes of embodiment 2. The micropipe groups are arranged in a ring. All of these micropipes are arranged radially, and the closed end of the micropipe is arranged in the lateral side of the micropipe. The micropipes are radially distributed according to the center of centrifugation on a plane.

Embodiment 7 Detection Method of Human ABO Blood Group Positive Typing and Rh(D) Blood Group Microfluidic Reagent Card A detection method of the human ABO blood group positive typing and Rh(D) blood group microfluidic reagent card according to embodiment 5, comprising the following steps:

1) Take out the microfluidic reagent card, and balance the microfluidic reagent card to room temperature;
2) Mark the microfluidic reagent card, remove the sealing material, avoid cross-contamination, and place the microfluidic reagent card in the centrifugation device;
3) Load sample of whole blood and centrifuge;
4) Read the testing result from a detection window.

Embodiment 8 ABO Blood Group Positive Typing and Rh(D) Blood Group Microfluidic Reagent Card for Newborns An ABO blood group positive typing and Rh(D) blood group microfluidic reagent card for newborns, with reference to FIG. 4, comprises a card body and a plurality of micropipes, the plurality of micropipes is fixed onto the card body. The plurality of micro cubes is divided into 12 groups, each group has 6 micropipes. The micropipes are arranged radially, and radially distributed according to the center of centrifugation on a plane; the microfluidic reagent card also comprises an automatic quantitative sample distribution device. The micropipe is connected to an automatic quantitative sample distribution device. The automatic quantitative sample distribution device comprises a sample adding component and a plurality of quantitative sample distribution systems. A micropipe gel separation device is used to separate agglutinated from non-agglutinated red blood cells. A predetermined amount of sample enters into the connected micropipe gel separation device, which separates agglutinated from non-agglutinated red blood cells.

The separation medium layer in the micropipe are gel particles;

The detection liquid layers in each group of 6 micropipes are:

| Micropipe No. | Component Description |
|---|---|
| Micropipe 1: anti-A reagent | anti-A mouse monoclonal (IgM) antibody (clone BRIMA-1) |
| Micropipe 2: anti-B reagent | anti-B mouse monoclonal (IgM) antibody (clone LB-2) |
| Micropipe 3: anti-AB reagent | anti-B mouse monoclonal (IgM) antibody (clone ES-4) anti-A(B) mouse monoclonal (IgM) antibody (clone ES-15) |
| Micropipe 4: anti-Rh(D) reagent | Anti-Rh(D) human monoclonal (IgM) antibody (clone RUM-1) |
| Micropipe 5: control reagent | Antibody diluent |
| Micropipe 6: anti-human globulin reagent | Goat anti-human IgG antibody |

Embodiment 9 Detection Method of ABO Blood Group Positive Typing and Rh(D) Blood Group Microfluidic Reagent Card for Newborns As described in Embodiment 8, detection method of ABO blood group positive typing and Rh(D) blood group microfluidic reagent card for newborns comprises the following steps:

1) Take out the microfluidic reagent card, and balance the microfluidic reagent card to room temperature;
2) Mark the microfluidic reagent card, remove the sealing material, avoid cross-contamination, and place the microfluidic reagent card in the centrifugal device;
3) Load sample of whole blood;
4) Centrifuge;
5) Read the testing result from a detection window.

Embodiment 10 A Microfluidic Reagent Card for Human Rh System Typing

A Microfluidic reagent card for human Rh system typing, with reference to FIG. 4, comprises a card body and a plurality of micropipes, the plurality of micropipes is fixed on the card body. The plurality of micro cubes is divided into 12 groups, each group has 6 micropipes. The micropipes are arranged radially, and radially distributed according to the center of centrifugation on a plane. The microfluidic reagent card also comprises automatic quantitative sample distribution device. The micropipe is connected to an automatic quantitative sample distribution device, the automatic quantitative sample distribution device comprises a sample adding component and a plurality of quantitative sample distribution systems, the micropipe gel separation device is used to separate agglutinated from non-agglutinated red blood cells, a predetermined amount of sample enters into the connected micropipe gel separation device, which separates agglutinated from non-agglutinated red blood cells.

The separation medium layer in the micropipe are gel particles.

The detection liquid layers in each group of 6 micropipes are:

| Micropipe No. | Component Description |
|---|---|
| Micropipe 1: anti-C reagent | Anti-C antibody human monoclonal (IgM) antibody (clone MS-24) |
| Micropipe 2: anti-c reagent | Anti-c antibody human monoclonal (IgM) antibody (clone MS-33) |
| Micropipe 3: anti-D reagent | Anti-Rh(D) human monoclonal (IgM) antibody (clone RUM-1) |
| Micropipe 4: anti-E reagent | Anti-E antibody human monoclonal (IgM) antibody (clone MS-80/MS-258) |
| Micropipe 5: anti-e reagent | Anti-e antibody human monoclonal (IgM) antibody (clone MS-16/MS-21/MS-63) |
| Micropipe 6: control reagent | Antibody diluent |

Embodiment 11 Detection Method of a Microfluidic Reagent Card for Human Rh System Typing A detection method of a microfluidic reagent card for human Rh system typing according to embodiment 10 comprises the following steps:
1) Take out the microfluidic reagent card, and balance the microfluidic reagent card to room temperature;
2) Mark the microfluidic reagent card, remove the sealing material, avoid cross-contamination, and place the microfluidic reagent card in the centrifugal device;
3) Load sample of whole blood;
4) Centrifuge;
5) Read the testing result from a detection window.

Finally, please note that, the embodiments above are intended to illustrate the specifics of the invention only, with no intention to limit the scope of the invention to these embodiments. Although the invention has been described in detail with references to the preferred embodiments above, a person skilled in the art would know that modifications or equivalent replacements without departing from the spirit and scope of the present invention shall still fall within the claimed scope of the present invention.

The invention claimed is:

1. A microfluidic reagent card, wherein comprising a card body and a micropipe, a plurality of the micropipes is fixed on the card body;
the micropipe is configured to have a sample inlet end and a closed end, and a detection liquid layer and a separation medium layer are arranged inside the micropipe in sequence from the sample inlet end to the closed end, wherein the separation medium layer is made of gel particles or glass beads, the micropipe has a diameter of 0.1-1.0 mm, wherein a reduced fluidity of a liquid in the micropipe forms a liquid interface holding the separation medium layer in place;
the sample inlet end is configured to be connected to an automatic quantitative sample distribution device, and a sample is added into the plurality of the micropipes simultaneously;
the automatic quantitative sample distribution device comprises a sample adding component, the sample adding component is connected to a quantitative region, the quantitative region is connected to the sample inlet, a closing portion is provided between the quantitative region and the sample inlet end of the micropipe.

2. The microfluidic reagent card according to claim 1, wherein the detection liquid layer comprises a diluent, the diluent comprises an antibody reagent or does not comprise any antibody reagent.

3. The microfluidic reagent card according to claim 1, wherein the plurality of the micropipes is arranged radially, the closed end of each of the plurality of the micropipes is arranged at the lateral side of the micropipe.

4. The microfluidic reagent card according to claim 1, wherein the automatic quantitative sample distribution device comprises a sample adding component and a plurality of quantitative sample distribution systems.

5. A detection method using the microfluidic reagent card according to claim 1, wherein the detection method comprises the following steps: entering a sample into the micropipe to be mixed with the detection liquid layer in the micropipe, centrifuging the micropipe, and reading a result.

6. A detection method for detecting an antigen-antibody reaction using the microfluidic reagent card according to claim 1, wherein the detection method comprises the following steps: entering a sample into the micropipe to be mixed with the detection liquid layer in the micropipe, centrifuging the micropipe, and reading a result of an antigen-antibody reaction.

7. The detection method for detecting an antigen-antibody reaction using the microfluidic reagent card according to claim 6, wherein the sample and the detection liquid layer are selected for detecting a reaction from a group consisting of blood grouping, antibody screening and cross-matching of blood.

* * * * *